United States Patent
Castinado et al.

(10) Patent No.: US 10,456,054 B2
(45) Date of Patent: Oct. 29, 2019

(54) ELECTROENCEPHALOGRAM TRIGGERED RESOURCE DISTRIBUTION QUERY SYSTEM

(71) Applicant: BANK OF AMERICA CORPORATION, Charlotte, NC (US)

(72) Inventors: Joseph Benjamin Castinado, North Glenn, CO (US); Charles Russell Kendall, Snoqualmie, WA (US)

(73) Assignee: BANK OF AMERICA CORPORATION, Charlotte, NC (US)

( * ) Notice: Subject to any disclaimer, the term of this patent is extended or adjusted under 35 U.S.C. 154(b) by 199 days.

(21) Appl. No.: 15/802,034

(22) Filed: Nov. 2, 2017

(65) Prior Publication Data

US 2019/0125203 A1 May 2, 2019

(51) Int. Cl.
| | | |
|---|---|---|
| A61B 5/04 | (2006.01) | |
| A61B 5/00 | (2006.01) | |
| A61B 5/0476 | (2006.01) | |
| G06F 16/27 | (2019.01) | |
| G06F 16/2457 | (2019.01) | |

(52) U.S. Cl.
CPC ........ *A61B 5/04012* (2013.01); *A61B 5/0476* (2013.01); *A61B 5/746* (2013.01); *G06F 16/24575* (2019.01); *G06F 16/27* (2019.01)

(58) Field of Classification Search
CPC ........... A61B 5/04; A61B 5/00; A61B 5/0476; A61B 5/04012; A61B 5/746; G06F 16/24575; G06F 16/27; G06F 3/015; G06K 9/00523; G06K 2009/00939; H04L 63/0861; A61M 2230/10
See application file for complete search history.

(56) References Cited

U.S. PATENT DOCUMENTS

| | | |
|---|---|---|
| 3,848,586 A | 11/1974 | Suzuki et al. |
| 5,495,853 A | 3/1996 | Yasushi |
| (Continued) | | |

OTHER PUBLICATIONS

Ruiz-Blondet et al., "CEREBRE: A Novel Method for Very High Accuracy Event-Related Potential Biometric Identification," IEEE Transactions on Information Forensics and Security, vol. 11, No. 7, Jul. 2016 (Year: 2016).*

(Continued)

*Primary Examiner* — Eric J Messersmith
(74) *Attorney, Agent, or Firm* — Michael A. Springs; Moore & Van Allen PLLC; Nicholas C. Russell

(57) ABSTRACT

Embodiments of the invention are directed to systems, methods, and computer program products for electroencephalogram triggered resource distribution query. In this way, the system may generate a spectral analysis baseline electroencephalogram reading for a user that can be segmented and analyzed based on a specific time span associated with a known stimulus or event, and diagnostic applications generally focus on either event-related potentials or the like. The system may utilize EEG recognition to identify a user baseline and for tiered velocity/frequency tolerance identification of resource distribution. In this way, based on a tiered velocity/frequency tolerances of the user or the resource distribution system, the user may be alerted of an action control network for management of the resource distribution upon an EEG reading during initiation of the resource distribution.

20 Claims, 5 Drawing Sheets

(56) References Cited

U.S. PATENT DOCUMENTS

| | | |
|---|---|---|
| 5,626,145 A | 5/1997 | Clapp et al. |
| 5,687,291 A | 11/1997 | Smyth |
| 6,021,346 A | 2/2000 | Ryu et al. |
| 6,092,058 A | 7/2000 | Smyth |
| 6,317,627 B1 | 11/2001 | Ennen et al. |
| 6,488,617 B1 | 12/2002 | Katz |
| 6,496,724 B1 | 12/2002 | Levendowski et al. |
| 6,735,467 B2 | 5/2004 | Wilson |
| 7,035,685 B2 | 4/2006 | Ryu et al. |
| 7,299,088 B1 | 11/2007 | Thakor et al. |
| 8,135,957 B2 | 3/2012 | Dinges et al. |
| 8,457,595 B2 | 6/2013 | MacInnis et al. |
| 9,268,876 B2 | 2/2016 | MacInnis et al. |
| 9,473,493 B2 | 10/2016 | Jayaraman et al. |
| 10,154,818 B2 | 12/2018 | Zhang et al. |
| 10,176,894 B2 | 1/2019 | Park et al. |
| 2004/0077966 A1 | 4/2004 | Yamaguchi et al. |
| 2004/0077967 A1 | 4/2004 | Jordan |
| 2005/0085872 A1 | 4/2005 | Yanagihara et al. |
| 2006/0135879 A1 | 6/2006 | Liley |
| 2010/0191140 A1 | 7/2010 | Terada et al. |
| 2010/0317988 A1 | 12/2010 | Terada et al. |
| 2011/0071416 A1 | 3/2011 | Terada et al. |
| 2012/0108995 A1* | 5/2012 | Pradeep ............ A61B 5/0476 600/544 |
| 2014/0159862 A1 | 6/2014 | Yang et al. |
| 2014/0178843 A1 | 6/2014 | Smyth |
| 2015/0081226 A1 | 3/2015 | Baki |
| 2015/0294085 A1 | 10/2015 | Kare et al. |
| 2016/0004862 A1 | 1/2016 | Almehmad et al. |
| 2016/0183812 A1 | 6/2016 | Zhang et al. |
| 2016/0188839 A1 | 6/2016 | Kaul et al. |
| 2017/0118204 A1 | 4/2017 | Laine et al. |
| 2017/0196501 A1 | 7/2017 | Watson et al. |
| 2017/0228512 A1 | 8/2017 | Driscoll |
| 2017/0323073 A1 | 11/2017 | Westermann et al. |

OTHER PUBLICATIONS

Ruiz-Blondet et al., "Permanence of the CEREBRE brain biometric protocol," Pattern Recognition Letters 95 (2017) 37-43 (Year: 2017).*

* cited by examiner

US 10,456,054 B2

ELECTROENCEPHALOGRAM TRIGGERED RESOURCE DISTRIBUTION QUERY SYSTEM

BACKGROUND

With advancements in technology, use of electroencephalography (EEG) and access to EEG devices are becoming more prevalent.

BRIEF SUMMARY

The following presents a simplified summary of one or more embodiments of the invention in order to provide a basic understanding of such embodiments. This summary is not an extensive overview of all contemplated embodiments, and is intended to neither identify key or critical elements of all embodiments, nor delineate the scope of any or all embodiments. Its sole purpose is to present some concepts of one or more embodiments in a simplified form as a prelude to the more detailed description that is presented later.

In some embodiments, the invention utilizes EEG data to trigger resource distribution queries to the user. In this way, the invention leverages EEG data or a user extracted from EEG devices to assist a user against third party pressures.

As such, the EEG data can be segmented and analyzed based on a specific time span associated with a known stimulus or event, and diagnostic applications generally focus on either event-related potentials (ERPs), some variation thereof, or on the spectral content of EEG. Data that is time-locked to complex processing of various stimuli may be referred to as an event-related potential, while a subclass of the EEG technique also include evoked potentials, or time-locked averages of EEG activity associated with presentation of a specific stimulus of some sort (auditory, visual, or somatosensory). The invention may determining what component frequencies are present in a specific user EEG response may involve computing a Fourier transform of a sampled user EEG signal. One can then resynthesize the sampled user EEG signal or compare subsequent signal analysis to detect similarities.

In some embodiments, the invention may also relate to an averaged ERP to provide accurate biometric information. One such method, cognitive event-related biometric recognition (CEREBRE) protocol allows for 100% identification accuracy utilizing individually unique responses from multiple functional brain systems, such as the primary visual, facial recognition, and gustatory/appetitive systems. Some embodiments of the invention may incorporate such methods in order to leverages EEG data or a user extracted from EEG devices to assist a user against third party pressures.

Embodiments of the invention relate to systems, methods, and computer program products for EEG triggered resource distribution action control, the invention comprising identifying a transmission from an EEG reader for establishing a baseline EEG reading for the user; identifying a transmission from the EEG reader for establishing a velocity tolerance EEG reading; storing the baseline EEG reading for the user and the velocity tolerance EEG reading for the user in a user EEG profile; identifying the user requesting resource distribution; locating an EEG reader at a location associated with the resource distribution and form a communicable linkage with the EEG reader at the location associated with the resource distribution; receiving an EEG reading from the EEG reader at the location associated with the resource distribution; performing comparative spectral analysis to the EEG reading from the EEG reader at the location associated with the resource distribution; plotting, using an EEG reading continuum, the EEG reading from the EEG reader at the location associated with the resource distribution with respect to the user baseline EEG reading and velocity tolerance EEG reading; and triggering action control alert distribution to a user device associated with the user upon indication of the EEG reading from the EEG reader at the location associated with the resource distribution is between the baseline EEG reading and a high velocity tolerance EEG reading on the EEG reading continuum.

In some embodiments, the invention further comprising denying and preventing a transmission of the resource distribution based on no user acknowledgement of the action control alert.

In some embodiments, the invention further comprising generating the EEG reading continuum between the baseline EEG reading for the user and velocity tolerance EEG reading for the user.

In some embodiments, the velocity tolerance EEG reading is an EEG reading of a user at a high and low tolerance level for resource distribution during periods of purchasing of one or more categories of products or services and an amount of resources or frequency of distribution exceeding user tolerances.

In some embodiments, establishing the velocity tolerance EEG reading for the user further comprises compiling EEG data during high and low tolerance level resource distribution periods and performing spectral analysis to establish the velocity tolerance EEG reading, wherein spectral analysis comprises generating a cognitive event-related biometric recognition protocol for a late potential of the EEG reading.

In some embodiments, establishing a baseline EEG reading for the user further comprises compiling EEG data from the baseline EEG reading and performing spectral analysis to establish the baseline EEG reading, wherein spectral analysis comprises generating a cognitive event-related biometric recognition protocol for a late potential of the EEG reading. In some embodiments, establishing a baseline EEG reading for the user further comprises transmitting one or more known stimuli to the user for EEG reading of user reaction to the known stimuli to determine the user reaction to standard category resource distribution for the user.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Figure 1:
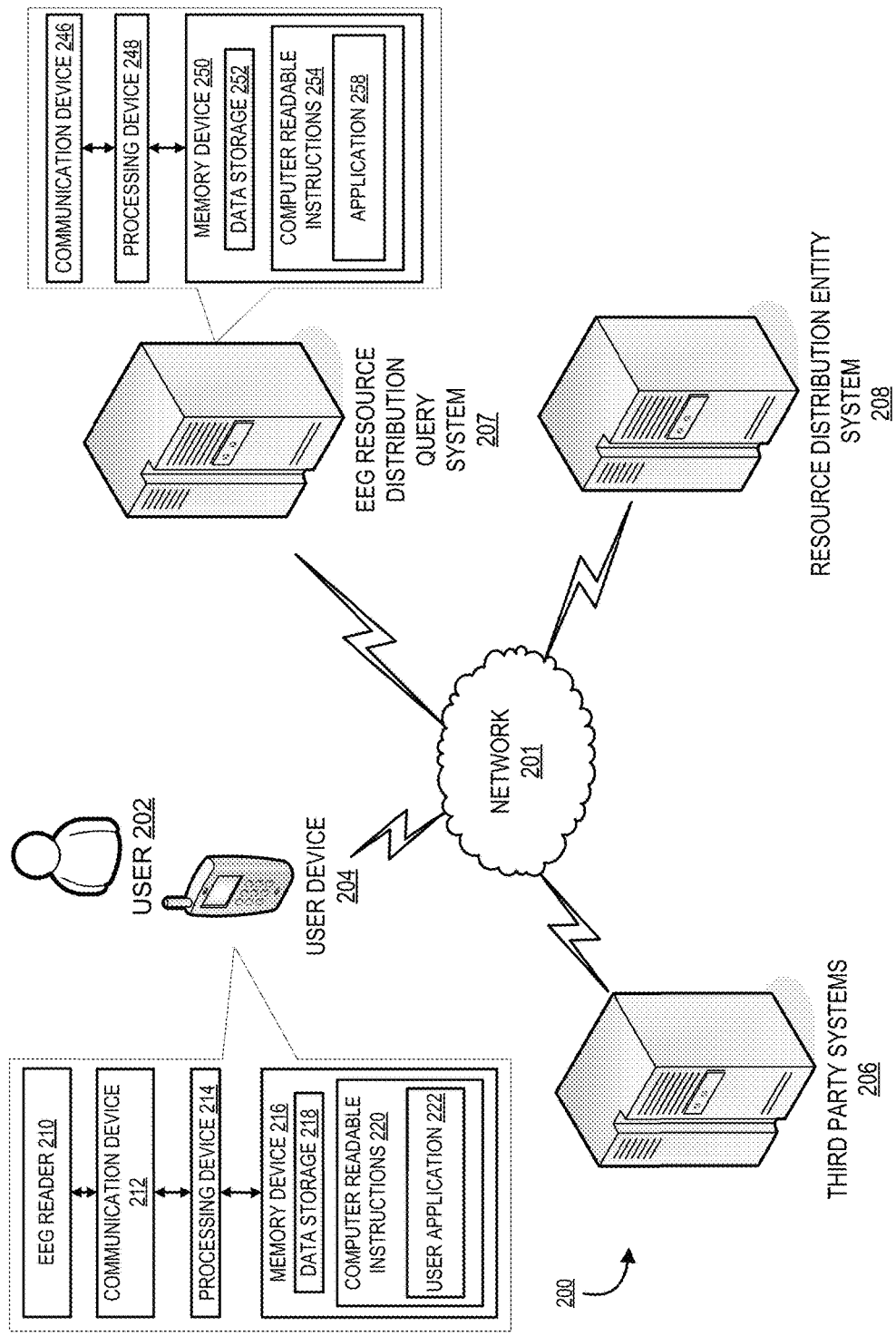
Figure 2:
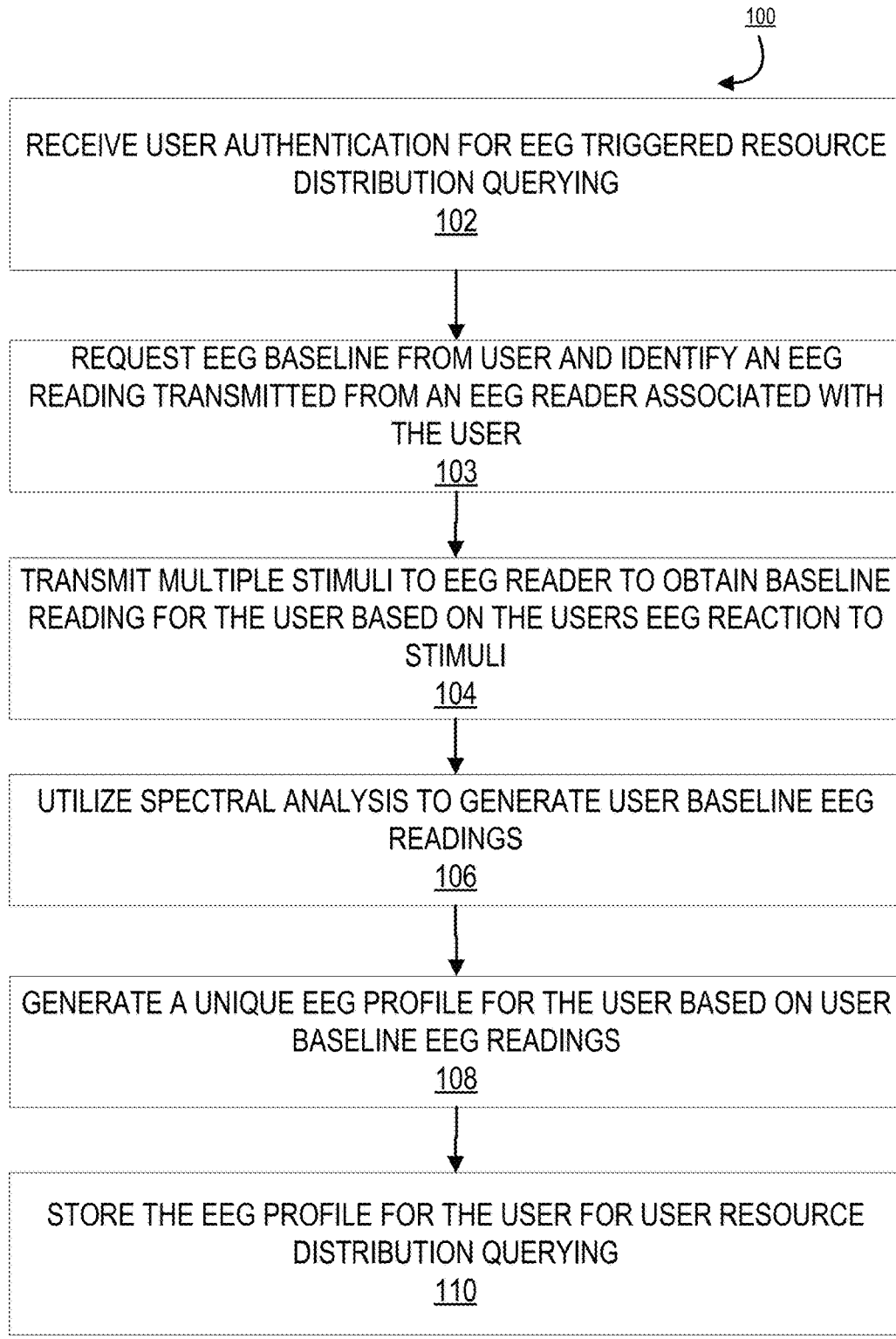
Figure 3:
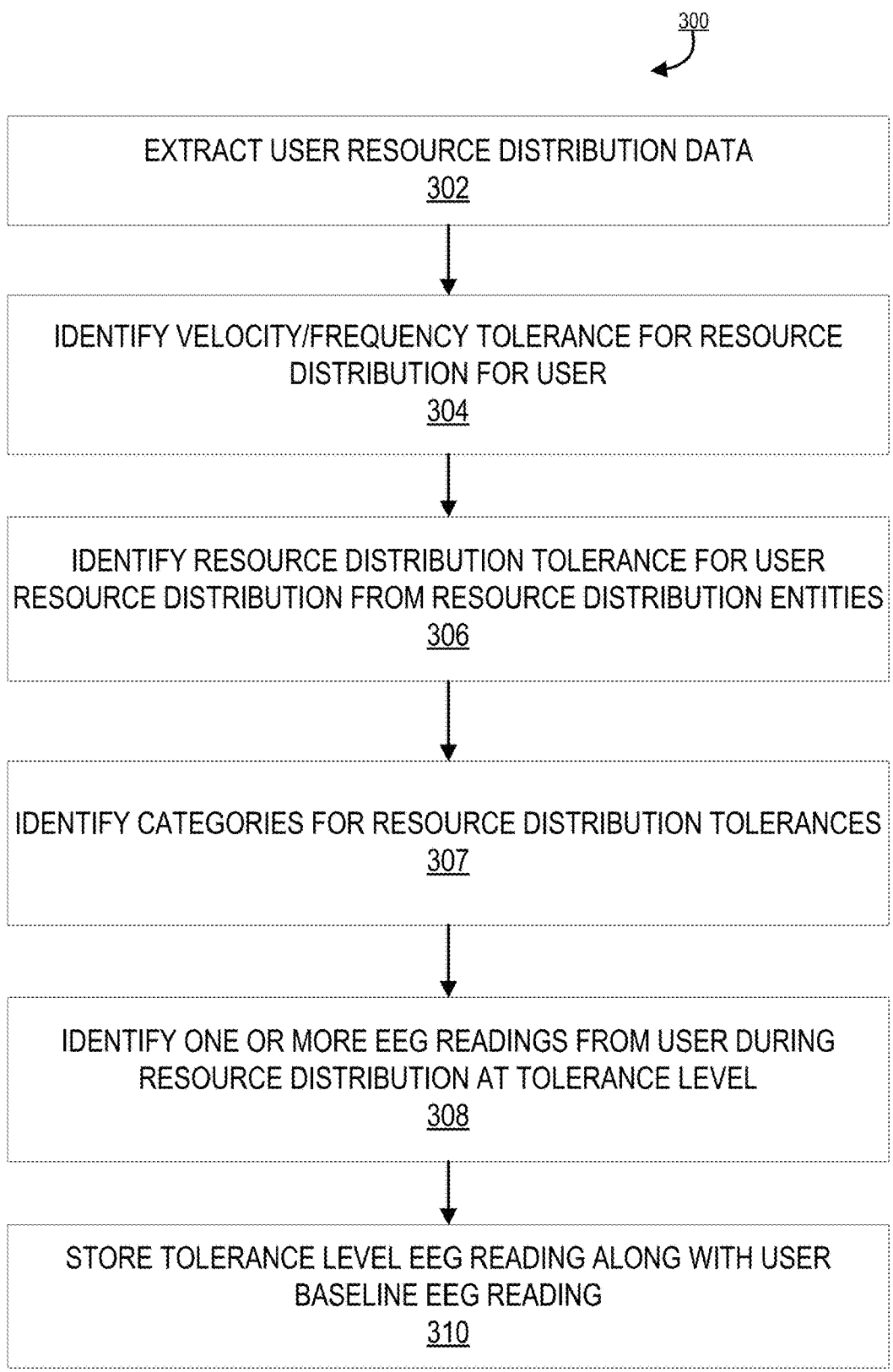
Figure 4:
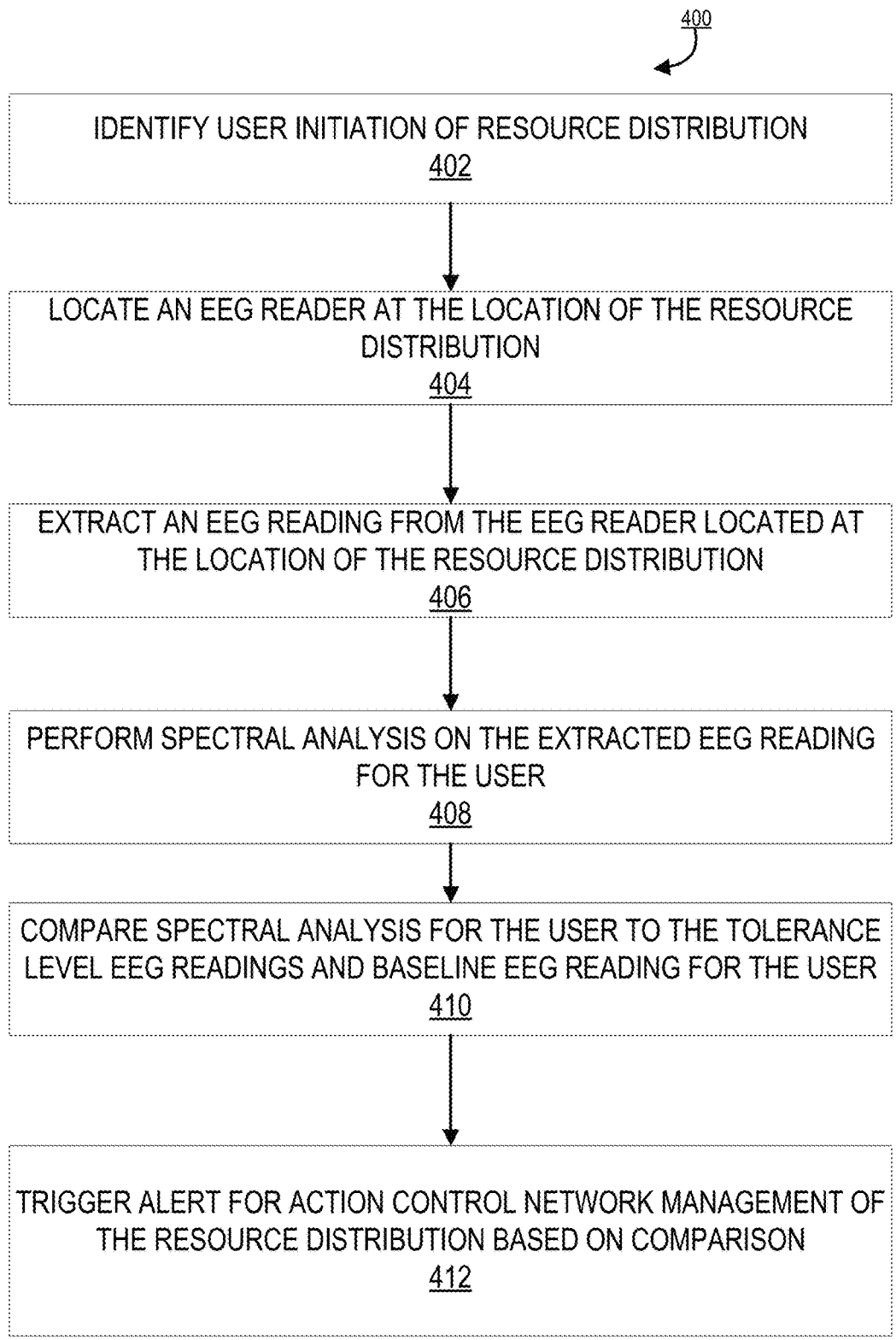
Figure 5:
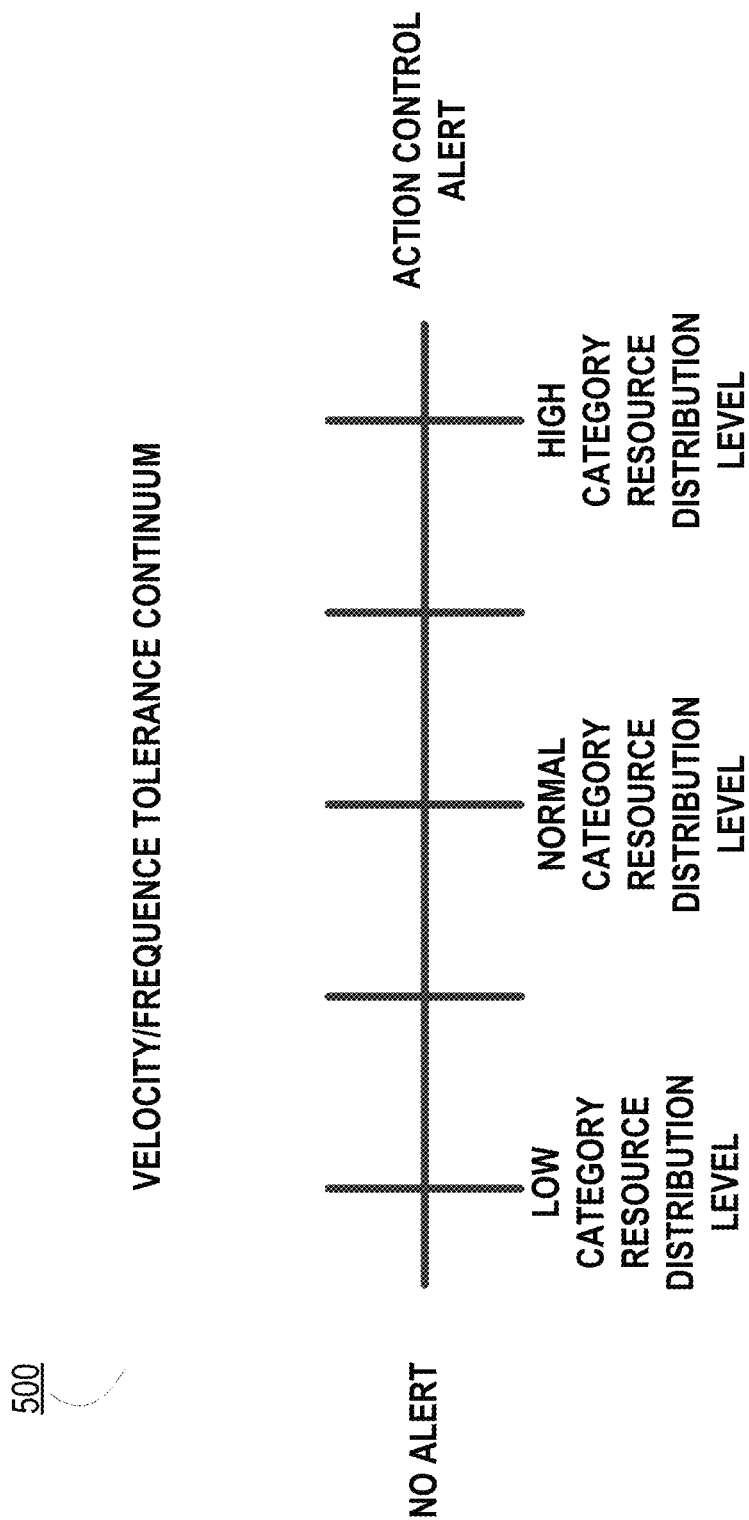

Having thus described embodiments of the invention in general terms, reference will now be made to the accompanying drawings, where:

FIG. 1 illustrates an EEG triggered resource distribution query system environment, in accordance with embodiments of the present invention;

FIG. 2 illustrates a high level flowchart for EEG triggered resource distribution query process, in accordance with embodiments of the present invention;

FIG. 3 illustrates a flow chart for EEG triggered resource distribution query initiation processing, in accordance with embodiments of the present invention;

FIG. 4 illustrates a flow chart for EEG triggered resource distribution query activation of an action control network, in accordance with embodiments of the present invention; and FIG. 5 illustrates a velocity/frequency EEG triggering continuum, in accordance with embodiments of the present invention.

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to elements throughout. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein.

In some embodiments, an "entity" may be a financial institution or third party merchant. For the purposes of this invention, a "financial institution" may be defined as any organization, entity, or the like in the business of moving, investing, or lending money, dealing in financial instruments, or providing financial services. This may include commercial banks, thrifts, federal and state savings banks, savings and loan associations, credit unions, investment companies, insurance companies and the like. In some embodiments, the entity may allow a user to establish an account with the entity. An "account" may be the relationship that the user has with the entity. Examples of accounts include a deposit account, such as a transactional account (e.g., a banking account), a savings account, an investment account, a money market account, a time deposit, a demand deposit, a pre-paid account, a credit account, a non-monetary user profile that includes only personal information associated with the user, or the like. The account is associated with and/or maintained by the entity. In other embodiments, an entity may not be a financial institution. In still other embodiments, the entity may be the merchant itself.

A "transaction" or "resource distribution" refers to any communication between a user and the financial institution or other entity monitoring the user's activities to transfer funds for the purchasing or selling of a product. A transaction may refer to a purchase of goods or services, a return of goods or services, a payment transaction, a credit transaction, or other interaction involving a user's account. In the context of a financial institution, a transaction may refer to one or more of: a sale of goods and/or services, initiating an automated teller machine (ATM) or online banking session, an account balance inquiry, a rewards transfer, an account money transfer or withdrawal, opening a bank application on a user's computer or mobile device, a user accessing their e-wallet, or any other interaction involving the user and/or the user's device that is detectable by the financial institution. A transaction may include one or more of the following: renting, selling, and/or leasing goods and/or services (e.g., groceries, stamps, tickets, DVDs, vending machine items, and the like); making payments to creditors (e.g., paying monthly bills; paying federal, state, and/or local taxes; and the like); sending remittances; loading money onto stored value cards (SVCs) and/or prepaid cards; donating to charities; and/or the like. In some embodiments, the invention may authorize or allow a user access to one or more websites, physical locations, secure locations, accounts, interfaces, or the like.

Embodiments of the invention are directed to systems, methods, and computer program products for electroencephalogram triggered resource distribution query. In this way, the system may generate a spectral analysis baseline electroencephalogram reading for a user that can be segmented and analyzed based on a specific time span associated with a known stimulus or event, and diagnostic applications generally focus on either event-related potentials or the like. The system may utilize EEG recognition to identify a user baseline and for tiered velocity/frequency tolerance identification of resource distribution. In this way, based on a tiered velocity/frequency tolerances of the user or the resource distribution system, the user may be alerted of an action control network for management of the resource distribution upon an EEG reading during initiation of the resource distribution.

In some embodiments, the invention associated with an electroencephalogram (EEG) which is a monitoring method to record electrical activity of the brain. EEG measures voltage fluctuations resulting from ionic current with neurons of the brain. In this way, the EEG refers to the recording of the brain's electrical activity over a period of time. In some embodiments, an EEG may be used to identify a user based on tracking the EEG of the user and generating a baseline EEG for the user. This may be used to identify the user and identify potential high stress or high pressure resource distribution situations based on tiered velocity/frequency tolerances of the user or the resource distribution system. In this way, the invention leverages EEG data or a user extracted from EEG devices to assist a user against third party pressures.

In this way, the invention interconnects with a network for real-time data transfer from user devices, third party devices, and other connected devices to receive, analyze, and react to electroencephalography data. As such, upon receiving and analyzing specific user based electroencephalography data, the system may form and activate a user specific electroencephalography profile and send control signals across a network for user authentication.

In some embodiments, the invention utilizes a brain computer interface (BCI), or a direct communication pathway between an enhanced or wired brain and an external device. EEG is a monitoring method to record electrical activity of the brain, and is one of the most studied non-invasive approaches to brain computer interfacing, mainly due to its fine temporal resolution, ease of use, portability, and low set-up cost. Typically completely non-invasive, existing EEG technology may involve placing a number of electrodes along the scalp to measure voltage fluctuations resulting from ionic current within the neurons of the brain; however, modern research indicates that EEG devices may become smaller, more portable and easier to use, and embodiments of the present invention contemplate the use of such "wearable EEG" electronics which utilize a low power wireless connection and "dry" electrodes which are characterized by their lack of need for conductive gel during use.

EEG data can be segmented and analyzed based on a specific time span associated with a known stimulus or event, and diagnostic applications generally focus on either event-related potentials (ERPs), some variation thereof, or on the spectral content of EEG. Data that is time-locked to complex processing of various stimuli may be referred to as an event-related potential, while a subclass of the EEG technique also include evoked potentials, or time-locked averages of EEG activity associated with presentation of a specific stimulus of some sort (auditory, visual, or somatosensory). Spectral analysis is a method for the study of EEG signals, and specifically involves the study of neural oscillations, more commonly known as brain waves, that can be observed in EEG signals in the frequency domain. Through statistical analysis and signal processing, the frequency content of EEG signals can be characterized, and periodicities can be detected in the data by observing peaks at the sequences corresponding to these periodicities. Determining what component frequencies are present in a specific user EEG response may involve computing a Fourier transform of a sampled user EEG signal. One can then resynthesize the sampled user EEG signal or compare subsequent signal analysis to detect similarities.

EEG measures voltage fluctuations resulting from ionic current within the neurons of the brain, and in clinical contexts, EEG refers to the recording of the brain's spontaneous electrical activity over a period of time. EEG has very high temporal resolution, on the order of milliseconds, and EEG signals are commonly recorded at sampling rates between 250 and 2000 Hz in clinical and research settings, while modern EEG data collection systems are capable of recording at sampling rates even above 20,000 Hz if so desired. EEG is relatively tolerant of subject movement, unlike most other neuroimaging techniques, and operation of EEG devices is silent, allowing for study of responses to auditory stimuli without the introduction of noise into the EEG signal. Detection of cover brain processing is possible with EEG, meaning that processing does not require a physical response to be registered by an EEG system and allowing for the use of EEG by users who are incapable of making a motor response.

One variation of ERP, known as the P300 response is characterized as a "late" potential, as it occurs at 300-800 milliseconds after the associated stimulus, and it is also known as the P3, N2-P3 complex, P3a and P3b, late positive complex, and LPC. P300, refers to the electrically positive character of the response as well as the latency of greater than or equal to 300 milliseconds. The P300 may either be a unitary response or a part of a larger grouping of several responses such as the memory and encoding related multifaceted electroencephalographic response, or P300-MERMER. Embodiments of the present invention utilizes one or more of these responses in order to establish an objective method of brain fingerprinting, wherein brain responses to known stimuli are detected, quantified, and analyzed to determine whether or not a user knows critical information. Brain fingerprinting systems are able to compute, with a statistical confidence of 99.9%, a determination of whether or not a user knows critical information presented.

In some embodiments, the invention may also relate to an averaged ERP to provide accurate biometric information. One such method, cognitive event-related biometric recognition (CEREBRE) protocol allows for 100% identification accuracy utilizing individually unique responses from multiple functional brain systems, such as the primary visual, facial recognition, and gustatory/appetitive systems. These results indicate a method of user identification of users via the collection and analysis of EEG readings. Some embodiments of the invention may incorporate such methods in order to identify users with a high degree of accuracy, and may associate this identification information with a larger profile on the user that contains stored user preferences and demographics. The combined use of the P300 type response analysis, CEREBRE protocol biometric information, and stored user preference and user demographic information allows embodiments of the invention to build a complete picture of who the user is, what they know, what they prefer, and how they are reacting in real-time. The system may react to this known user information according to a set protocol or operator instructions to authorize a user for access to one or more locations.

FIG. 1 illustrates an EEG triggered resource distribution query system environment 200, in accordance with embodiments of the present invention. FIG. 1 provides the system environment 200 for which the distributive network system with specialized data feeds for EEG recognition for tiered velocity/frequency tolerance identification and querying for user resource distribution. FIG. 1 provides a unique system that includes specialized servers and system communicably linked across a distributive network of nodes required to perform the functions of EEG recognition for tiered velocity/frequency tolerance identification and querying for user resource distribution.

As illustrated in FIG. 1, the resource distribution entity system 208 is operatively coupled, via a network 201 to the user device 204, EEG resource distribution query system 207, and to the third party systems 206. In this way, the resource distribution entity system 208 can send information to and receive information from the user device 204, EEG resource distribution query system 207, and the third party systems 206. FIG. 1 illustrates only one example of an embodiment of the system environment 200, and it will be appreciated that in other embodiments one or more of the systems, devices, or servers may be combined into a single system, device, or server, or be made up of multiple systems, devices, or servers.

The network 201 may be a system specific distributive network receiving and distributing specific network feeds and identifying specific network associated triggers. The network 201 may also be a global area network (GAN), such as the Internet, a wide area network (WAN), a local area network (LAN), or any other type of network or combination of networks. The network 201 may provide for wireline, wireless, or a combination wireline and wireless communication between devices on the network 201.

In some embodiments, the user 202 is one or more individuals authenticating into an account, device, system, network, or the like. The user may have one or more accounts associated with resources for distribution of the resources. FIG. 1 also illustrates a user device 204. The user device 204 may be, for example, a desktop personal computer, business computer, business system, business server, business network, a mobile system, such as a cellular phone, smart phone, personal data assistant (PDA), laptop, or the like. The user device 204 generally comprises a communication device 212, a processing device 214, and a memory device 216. The processing device 214 is operatively coupled to the communication device 212 and the memory device 216. The processing device 214 uses the communication device 212 to communicate with the network 201 and other devices on the network 201, such as, but not limited to the third party systems 206, the resource distribution entity system 208, and the EEG resource distribution query system 207. As such, the communication device 212 generally comprises a modem, server, or other device for communicating with other devices on the network 201.

The user device 204 comprises computer-readable instructions 220 and data storage 218 stored in the memory device 216, which in one embodiment includes the computer-readable instructions 220 of a user application 222. In some embodiments, the user application 222 allows a user 202 to set up marker codes and communicate with the third party systems 206.

Furthermore, the user device 204 may comprise an EEG reader 210. An EEG reader 210 is a monitoring method to record electrical activity of the brain. EEG measures voltage fluctuations resulting from ionic current with neurons of the brain. In this way, the EEG refers to the recording of the brain's electrical activity over a period of time. In some embodiments, an EEG may be used to identify a user based on tracking the EEG of the user and generating a baseline EEG for the user.

As further illustrated in FIG. 1, the EEG resource distribution query system 207 generally comprises a communication device 246, a processing device 248, and a memory device 250. As used herein, the term "processing device" generally includes circuitry used for implementing the communication and/or logic functions of the particular system. For example, a processing device may include a digital signal processor device, a microprocessor device, and various analog-to-digital converters, digital-to-analog converters, and other support circuits and/or combinations of the foregoing. Control and signal processing functions of the system are allocated between these processing devices according to their respective capabilities. The processing device may include functionality to operate one or more software programs based on computer-readable instructions thereof, which may be stored in a memory device.

The processing device 248 is operatively coupled to the communication device 246 and the memory device 250. The processing device 248 uses the communication device 246 to communicate with the network 201 and other devices on the network 201, such as, but not limited to the resource distribution entity system 208, the third party systems 206, and the user device 204. As such, the communication device 246 generally comprises a modem, server, or other device for communicating with other devices on the network 201.

As further illustrated in FIG. 1, the EEG resource distribution query system 207 comprises computer-readable instructions 254 stored in the memory device 250, which in one embodiment includes the computer-readable instructions 254 of an application 258. In some embodiments, the memory device 250 includes data storage 252 for storing data related to the system environment 200, but not limited to data created and/or used by the application 258.

In one embodiment of the EEG resource distribution query system 207 the memory device 250 stores an application 258. Furthermore, the EEG resource distribution query system 207, using the processing device 248 codes certain communication functions described herein. In one embodiment, the computer-executable program code of an application associated with the application 258 may also instruct the processing device 248 to perform certain logic, data processing, and data storing functions of the application. The processing device 248 is configured to use the communication device 246 to communicate with and ascertain data from one or more resource distribution entity system 208, EEG resource distribution query system 207, and/or user device 204.

In some embodiments, the EEG resource distribution query system 207 may analyze via spectral analysis or the like EEG data provided by one or more systems on the network and/or generated by the EEG resource distribution query system 207. In this way, the EEG resource distribution query system 207 may segment and analyze EEG data based on a specific time span associated with a known stimulus or event, and diagnostic applications generally focus on either event-related potentials (ERPs), some variation thereof, or on the spectral content of EEG.

In some embodiments, the EEG resource distribution query system 207 may utilize ERP such as a P300 response that occurs at 300-800 milliseconds after the associated stimulus that identifies electrically positive character of the response as well as the latency of greater than or equal to 300 milliseconds. In some embodiments, the EEG resource distribution query system 207 may utilize one or more of these responses in order to establish an objective method of brain fingerprinting, wherein brain responses to known stimuli are detected, quantified, and analyzed to determine whether or not a user knows critical information. Brain fingerprinting systems are able to compute, with a statistical confidence of 99.9%, a determination of whether or not a user knows critical information presented.

In other embodiments, the EEG resource distribution query system 207 may average ERP to provide accurate biometric information. In this way, the EEG resource distribution query system 207 may utilize cognitive event-related biometric recognition (CEREBRE) protocol for identification accuracy utilizing individually unique responses from multiple functional brain systems, such as the primary visual, facial recognition, and gustatory/appetitive systems. These results indicate a method of user identification of users via the collection and analysis of EEG readings. Some embodiments of the EEG resource distribution query system 207 may incorporate such methods in order to identify users with a high degree of accuracy, and may associate this identification information with a larger profile on the user that contains stored user preferences and demographics. The combined use of the P300 type response analysis, CEREBRE protocol biometric information, and stored user preference and user demographic information allows the EEG resource distribution query system 207 to build a complete picture of who the user is, what they know, what they prefer, and how they are reacting in real-time. The system may react to this known user information according to a set protocol or operator instructions to modify the user's experience based on a number of factors depending on the capabilities of the user device, third party device, or smart device with which the system is interfacing As illustrated in FIG. 1, the third party systems 206 is connected to the resource distribution entity system 208, user device 204, and EEG resource distribution query system 207. The third party systems 206 has the same or similar components as described above with respect to the user device 204 and the EEG resource distribution query system 207. In some embodiments, the third party systems 206 may further include an EEG reader. While only one third party system 206 is illustrated in FIG. 1, it is understood that multiple resource distribution entity system 208 may make up the system environment 200.

As illustrated in FIG. 1, the resource distribution entity system 208 is connected to the EEG resource distribution query system 207, user device 204, and third party systems 206. In other embodiments, the resource distribution entity system 208 may be a third party system separate from the EEG resource distribution query system 207. The resource distribution entity system 208 has the same or similar components as described above with respect to the user device 204 and the third party systems 206. While only one resource distribution entity system 208 is illustrated in FIG. 1, it is understood that multiple resource distribution entity system 208 may make up the system environment 200. In some embodiments, the resource distribution entity system 208 may further include an EEG reader.

In some embodiments, an EEG reader while illustrated with the user device 204 may also be associated with the third party systems 206, the EEG resource distribution query system 207, and/or the resource distribution entity system 208. The EEG reader is a monitoring method to record electrical activity of the brain.

It is understood that the servers, systems, and devices described herein illustrate one embodiment of the invention. It is further understood that one or more of the servers, systems, and devices can be combined in other embodiments and still function in the same or similar way as the embodiments described herein. The resource distribution entity system 208 may generally include a processing device communicably coupled to devices as a memory device, output devices, input devices, a network interface, a power source, one or more chips, and the like. The resource distribution entity system 208 may also include a memory device operatively coupled to the processing device. As used herein, memory may include any computer readable medium configured to store data, code, or other information. The memory device may include volatile memory, such as volatile Random Access Memory (RAM) including a cache area for the temporary storage of data. The memory device may also include non-volatile memory, which can be embedded and/or may be removable. The non-volatile memory may additionally or alternatively include an electrically erasable programmable read-only memory (EEPROM), flash memory or the like. The memory device may store any of a number of applications or programs which comprise computer-executable instructions/code executed by the processing device to implement the functions of the resource distribution entity system 208 described herein.

FIG. 2 illustrates a high level flowchart for EEG triggered resource distribution query process 100, in accordance with embodiments of the present invention. As illustrated in block 102, the process 100 is initiated by receiving user authentication for EEG triggered resource distribution querying. In this way, based on a tiered velocity/frequency tolerances of the user or the resource distribution system, the user may be alerted of an action control network for management of the resource distribution.

Upon receiving the request, the system may further request an EEG baseline from the user. As illustrated in block 103, upon request for an EEG baseline from the user, the system may identify an EEG reading transmitted from an EEG reader associated with the user.

In this way, the system may utilize a brain computer interface (BCI), or a direct communication pathway between an enhanced or wired brain and an external device such as the EEG reader or user device. EEG is a monitoring method to record electrical activity of the brain, and is a non-invasive approaches to brain computer interfacing, mainly due to its fine temporal resolution, ease of use, portability, and low set-up cost. EEG devices may be small portable and easier to use devices such as a wearable EEG device or EEG reader which utilize a low power wireless connection and dry electrodes which are characterized by their lack of need for conductive gel during use. These may be utilized by the user to determine a baseline EEG reading for the user.

The EEG data can be segmented and analyzed based on a specific time span associated with a known stimulus or event, and diagnostic applications generally focus on either ERPs, some variation thereof, or on the spectral content of EEG. Data that is time-locked to complex processing of various stimuli may be referred to as an event-related potential, while a subclass of the EEG technique also include evoked potentials, or time-locked averages of EEG activity associated with presentation of a specific stimulus of some sort (auditory, visual, or somatosensory). In some embodiments, the invention may use spectral analysis as a method for the study of EEG signals, which specifically involves the study of neural oscillations, more commonly known as "brain waves," that can be observed in EEG signals in the frequency domain. Through statistical analysis and signal processing, the frequency content of EEG signals can be characterized, and periodicities can be detected in the data by observing peaks at the sequences corresponding to these periodicities. Determining what component frequencies are present in a specific user EEG response may involve computing a Fourier transform of a sampled user EEG signal. One can then resynthesize the sampled user EEG signal or compare subsequent signal analysis to detect similarities.

One variation of ERP that the invention may involve is known as the P300 response. The P300 is characterized as a late potential, as it occurs at 300-800 milliseconds after the associated stimulus, and it is also known to those skilled in the art as the P3, N2-P3 complex, P3a and P3b, late positive complex, and LPC. P300 may either be a unitary response or a part of a larger grouping of several responses. Embodiments of the present invention may relate to a system that utilizes one or more of these responses in order to establish an objective method of brain fingerprinting, wherein brain responses to known stimuli are detected, quantified, and analyzed to determine whether or not a user has knowledge of critical information. Brain fingerprinting systems are able to compute a statistical confident determination of whether or not a user knows critical information presented.

Embodiments of the present invention may also utilize an averaged ERP to provide accurate biometric information and generate an EEG baseline for the user. One such method, known as the cognitive event-related biometric recognition (CEREBRE) protocol, utilizes individually unique responses from multiple functional brain systems, such as the primary visual, facial recognition, and gustatory/appetitive systems to generate unique EEG readings for a user. These results indicate a feasible method of user identification of users via the collection and analysis of EEG readings. Some embodiments of the invention may incorporate such methods in order to identify users with a high degree of accuracy, and may associate this identification information with a larger profile on the user that contains stored user preferences and demographics.

In some embodiments, the system may utilize a combined use of the P300 type response analysis, CEREBRE protocol biometric information, and stored user preferences to build an EEG baseline of the user.

As illustrated in block 104, the process 100 continues by transmitting multiple stimuli to the EEG reader to obtain the baseline reading for the user. These stimuli may include colors, pictures, videos, or the like and record the EEG readings from the user visualizing the one or more stimuli. As illustrated in block 106, the process 100 continues by utilizing spectral analysis to generate user baseline EEG readings. In some embodiments, the invention generates a user specific EEG profile in a user profile repository using EEG data collected from a user device containing an EEG reader. The user specific EEG profile includes the user EEG baseline. User specific EEG profile data is collected via a network and stored as a database of event-related potentials or evoked potentials corresponding to specific sets of stimuli, events, or triggers.

In this way, the invention interconnects with a network for real-time data transfer from user devices, third party devices, and other connected devices to receive, analyze, and react to EEG data from an EEG reader to allow generation of a determined user status within a user network account. In some embodiments, the user status may not be formally known to the user and may only be enacted when an institution confirms an external event is occurring or stimulus is present. When the status is enabled, the system may form and activate a first control signal to cause the EEG reader to capture subsequent EEG readings and react accordingly.

The system may further develop the user specific EEG profile corresponding to the user by analyzing predetermined attributes of the subsequent EEG signals and storing them as event-related potentials or evoked-potentials known to be associated with a particular user response. Analysis of the predetermined attributes of subsequent EEG readings may also allow the system to determine a user response based on a similarity between the analysis results and the same predetermined attributes for a known response. In this way, information received from the EEG reader can be used to determine when the user is present at a certain location, third party system, smart system, or other connected user device, and the subsequent EEG signals can be further analyzed against prior recorded event-related potentials to determine other attributes of the user's experience.

As illustrated in block 108, the user EEG profile may be generated based on the baseline EEG readings. Finally, as illustrated in block 110, the process 100 is completed upon storing the EEG profile for the user for user authentication.

FIG. 3 illustrates a flow chart for EEG triggered resource distribution query initiation processing 300, in accordance with embodiments of the present invention. As illustrated in block 302, the process 300 is initiated by extracting user resource distribution data. In this way, the system may identify the user historical tendencies in resource distribution to identify tolerances in resource distribution for purchase of a product or service.

Next, as illustrated in block 304, the process 300 continues by identifying velocity/frequency tolerances for resource distribution for the user. In this way, the invention identifies the tolerances for resource distribution, such as high amounts of resources the user may utilize for products or services. For example, the user may typically purchase meals for X.XX dollars, but there may be a few higher amounts or resources such as XXX.XX or the like that indicates an exception to the norm for the user meal purchases and indicates an tolerance level for the user for that category of resource distribution. Furthermore, the velocity or frequency of the purchases may suggest an adjusted tolerance for the user for resource distribution for a particular category.

As illustrated in block 306, the process 300 continues by identifying resource distribution tolerances for user resource distribution from the resource distribution entities. In this way, the system may communicate with resource distribution entity systems to identify an entity determined tolerance level for one or more resource distributions for products/services selected by the user.

Next as illustrated in block 307, the process 300 continues by identifying categories of products and/or services for resource distribution tolerances. In this way, the system may identify the products and/or services that the user typically spends resources on and determines categories of the products and/or services the user spends resources on. The system may identify one or more tolerances of the user for the various categories.

As illustrated in block 308, the process 300 continues by identifying one or more EEG readings from the user during resource distribution for the products and/or services at the tolerance level identified. In some embodiments, the EEG reader may be associated with the authentication location, such as an EEG reader integrated within a third party system, or the like. In some embodiments, the EEG reader may be a remote reader that is portable at the location. In some embodiments, the EEG reader may be associated with the user device.

The system may then form a communicable linkage with the one or more EEG readers identified at the resource distribution location. In this way, the system may integrate into the one or more EEG readers at resource distribution locations. The system may monitor the brain fingerprinting or spectral analysis of the user EEG at the time of the EEG reading from the user during the resource distribution for the products and/or services at or near the tolerance level that was previously identified.

As illustrated in block 310, the process 300 continues by storing the tolerance level EEG reading along with the user baseline EEG reading at the system. The tolerance level EEG and the baseline EEG reading may be processed via spectral analysis on the extracted EEG reading for the user. As discussed, the EEG reading data can be segmented and analyzed based on a specific time span associated with a known stimulus or event, and diagnostic applications generally focus on either ERPs, some variation thereof, or on the spectral content of EEG. Data that is time-locked to complex processing of various stimuli may be referred to as an event-related potential, while a subclass of the EEG technique also include evoked potentials, or time-locked averages of EEG activity associated with presentation of a specific stimulus of some sort (auditory, visual, or somatosensory). Spectral analysis is a method for the study of EEG signals, and specifically involves the study of neural oscillations, more commonly known as brain waves, that can be observed in EEG signals in the frequency domain. Through statistical analysis and signal processing, the frequency content of EEG signals can be characterized, and periodicities can be detected in the data by observing peaks at the sequences corresponding to these periodicities. Determining what component frequencies are present in a specific user EEG response may involve computing a Fourier transform of a sampled user EEG signal. One can then resynthesize the sampled user EEG signal or compare subsequent signal analysis to detect similarities.

One variation of ERP, known as the P300 response is characterized as a late potential, as it occurs at 300-800 milliseconds after the associated stimulus, and it is also known as the P3, N2-P3 complex, P3a and P3b, late positive complex, and LPC. P300, refers to the electrically positive character of the response as well as the latency of greater than or equal to 300 milliseconds. The P300 may either be a unitary response or a part of a larger grouping of several responses such as the memory and encoding related multifaceted electroencephalographic response, or P300-MERMER.

In some embodiments, the spectral analysis may also refer to an averaged ERP to provide accurate biometric information. One such method, cognitive event-related biometric recognition (CEREBRE) protocol is utilized for individually unique responses from multiple functional brain systems, such as the primary visual, facial recognition, and gustatory/appetitive systems. These results indicate a method of user identification of users via the collection and analysis of EEG readings. Some embodiments of the invention may incorporate such methods in order to identify users with a high degree of accuracy, and may associate this identification information with a larger profile on the user that contains stored user preferences and demographics.

FIG. 4 illustrates a flow chart for EEG triggered resource distribution query activation of an action control network 400, in accordance with embodiments of the present invention. As illustrated in block 402, the process 400 is initiated by identifying a user initiation of resource distribution. In some embodiments, resource distribution may include distribution of funds or currency for a product, service, or the like. The system may identify a user initiation of a resource distribution based on global positioning system (GPS) associated with the user device and co-located to a merchant or resource distribution location. In other embodiments, the system may be linked to the resource distribution entity and be able to identify an initiation of resource distribution based on a signal form the resource distribution entity. Furthermore, the system may identify an EEG reading from the user that may indicate a high pressure purchasing or compulsive identification. The system may use one or more of these processes for identification of the user initiation of the resource distribution.

Next, as illustrated in block 404, the process 400 continues by locating an EEG reader at the location of the resource distribution. In some embodiments, the EEG reader may be associated with the location, such as an EEG reader integrated within a third party system, or the like. In some embodiments, the EEG reader may be a remote reader that is portable at the location. In some embodiments, the EEG reader may be associated with the user device. The system may then form a communicable linkage with the one or more EEG readers identified at the location. In this way, the system may integrate into the one or more EEG readers at the location in order to activate and perform an EEG reading on the user. As illustrated in block 406, the system may extract an EEG reading from the EEG reader located at the location of the resource distribution.

Next, as illustrated in block 408, the process 400 continues by performing spectral analysis on the extracted EEG reading for the user. As discussed, the EEG reading data can be segmented and analyzed based on a specific time span associated with a known stimulus or event, and diagnostic applications generally focus on either ERPs, some variation thereof, or on the spectral content of EEG. Data that is time-locked to complex processing of various stimuli may be referred to as an event-related potential, while a subclass of the EEG technique also include evoked potentials, or time-locked averages of EEG activity associated with presentation of a specific stimulus of some sort (auditory, visual, or somatosensory). Spectral analysis is a method for the study of EEG signals, and specifically involves the study of neural oscillations, more commonly known as brain waves, that can be observed in EEG signals in the frequency domain. Through statistical analysis and signal processing, the frequency content of EEG signals can be characterized, and periodicities can be detected in the data by observing peaks at the sequences corresponding to these periodicities. Determining what component frequencies are present in a specific user EEG response may involve computing a Fourier transform of a sampled user EEG signal. One can then resynthesize the sampled user EEG signal or compare subsequent signal analysis to detect similarities.

One variation of ERP, known as the P300 response is characterized as a late potential, as it occurs at 300-800 milliseconds after the associated stimulus, and it is also known as the P3, N2-P3 complex, P3a and P3b, late positive complex, and LPC. P300, refers to the electrically positive character of the response as well as the latency of greater than or equal to 300 milliseconds. The P300 may either be a unitary response or a part of a larger grouping of several responses such as the memory and encoding related multi-faceted electroencephalographic response, or P300-MERMER.

In some embodiments, the spectral analysis may also refer to an averaged ERP to provide accurate biometric information. One such method, cognitive event-related biometric recognition (CEREBRE) protocol is utilized for individually unique responses from multiple functional brain systems, such as the primary visual, facial recognition, and gustatory/appetitive systems. These results indicate a method of user identification of users via the collection and analysis of EEG readings. Some embodiments of the invention may incorporate such methods in order to identify users with a high degree of accuracy, and may associate this identification information with a larger profile on the user that contains stored user preferences and demographics Next, as illustrated in block 410, the system may compare the EEG reading from the user at the location to the tolerance level EEG readings and user baseline EEG reading. In this way, the system may compare the tolerance level and baseline EEG reading to the user EEG reading at the location for identification of high pressure or velocity/frequency threshold tolerance being reached at the resource distribution location. The tolerance level EEG reading and the baseline EEG reading may have one or more variations due to various stimuli being introduced to the user during generation of the baseline EEG reading. The combined use of the P300 type response analysis, CEREBRE protocol biometric information, and stored user preference determine if a confidence match between the baseline EEG reading of the user and the EEG reading of the user at the location.

Next, as illustrated in block 412, the process 400 is completed by triggering an alert for action control network management of the resource distribution based on the comparison. In this way, if the EEG reading at the resource distribution location matches the tolerance level EEG readings or is located on the continuum between the baseline EEG reading and the tolerance level EEG reading, the system may trigger communication to the user device. The communication may request review of the resource distribution by the user via selection, clicking, swiping, or the like the user device. As such, requiring the user to perform an active function to stop the alert of the resource distribution. In this way, the system transmits an action control alert requiring user action for the management of the resource distribution in a situation of higher velocity or tolerance for the user.

Furthermore, in some embodiments, the system may deny or prevent the transmission of the resource distribution if the user has not approved or acknowledged the alert provided. As such, the system may communicate with the resource distribution entity to prevent or provide a stop payment to the resource distribution.

In some embodiments, the system may request or require a secondary authentication from a second authentication source, such as an individual associated with the user or the like.

FIG. 5 illustrates a velocity/frequency EEG triggering continuum 500, in accordance with embodiments of the present invention. The continuum aids in determining when the system sends an alert for action control management to the user. On the left-hand side of the continuum, a "no alert" is identified when no alert regarding action control needs to be transmitted to the user. On the right-hand side of the continuum, an "action control alert" requires full alert and active approval being provided to the user prior to completion of the resource distribution. As illustrated along the continuum, there is no alert required below the normal category resource distribution level, which corresponds to the user's baseline EEG reading for tolerance of purchasing a product or service within the category. If the user's EEG reading during the resource distribution is at or below the baseline EEG reading for that category, the system may transmit no action control alert to the user. As such, if the EEG reading is below the normal category resource distribution level or in the low category resource distribution level, no action control alert is transmitted. An action control alert is generated for any EEG readings along the continuum to the right of the normal category resource distribution level up to the high category resource distribution level, which is the user's EEG reading for velocity/frequency tolerance for that category resource distribution. If the EEG reading during the resource distribution is between the baseline EEG reading and the EEG reading for velocity/frequency tolerance the system transmits an action alert to the user for completion prior to the resource distribution.

As will be appreciated by one of ordinary skill in the art, the present invention may be embodied as an apparatus (including, for example, a system, a machine, a device, a computer program product, and/or the like), as a method (including, for example, a business process, a computer-implemented process, and/or the like), or as any combination of the foregoing. Accordingly, embodiments of the present invention may take the form of an entirely software embodiment (including firmware, resident software, microcode, and the like), an entirely hardware embodiment, or an embodiment combining software and hardware aspects that may generally be referred to herein as a "system." Furthermore, embodiments of the present invention may take the form of a computer program product that includes a computer-readable storage medium having computer-executable program code portions stored therein. As used herein, a processor may be "configured to" perform a certain function in a variety of ways, including, for example, by having one or more special-purpose circuits perform the functions by executing one or more computer-executable program code portions embodied in a computer-readable medium, and/or having one or more application-specific circuits perform the function. As such, once the software and/or hardware of the claimed invention is implemented the computer device and application-specific circuits associated therewith are deemed specialized computer devices capable of improving technology associated with the in authentication and instant integration of a new credit card to digital wallets.

It will be understood that any suitable computer-readable medium may be utilized. The computer-readable medium may include, but is not limited to, a non-transitory computer-readable medium, such as a tangible electronic, magnetic, optical, infrared, electromagnetic, and/or semiconductor system, apparatus, and/or device. For example, in some embodiments, the non-transitory computer-readable medium includes a tangible medium such as a portable computer diskette, a hard disk, a random access memory (RAM), a read-only memory (ROM), an erasable programmable read-only memory (EPROM or Flash memory), a compact disc read-only memory (CD-ROM), and/or some other tangible optical and/or magnetic storage device. In other embodiments of the present invention, however, the computer-readable medium may be transitory, such as a propagation signal including computer-executable program code portions embodied therein.

It will also be understood that one or more computer-executable program code portions for carrying out the specialized operations of the present invention may be required on the specialized computer include object-oriented, scripted, and/or unscripted programming languages, such as, for example, Java, Perl, Smalltalk, C++, SAS, SQL, Python, Objective C, and/or the like. In some embodiments, the one or more computer-executable program code portions for carrying out operations of embodiments of the present invention are written in conventional procedural programming languages, such as the "C" programming languages and/or similar programming languages. The computer program code may alternatively or additionally be written in one or more multi-paradigm programming languages, such as, for example, F#.

It will further be understood that some embodiments of the present invention are described herein with reference to flowchart illustrations and/or block diagrams of systems, methods, and/or computer program products. It will be understood that each block included in the flowchart illustrations and/or block diagrams, and combinations of blocks included in the flowchart illustrations and/or block diagrams, may be implemented by one or more computer-executable program code portions. These one or more computer-executable program code portions may be provided to a processor of a special purpose computer for the authentication and instant integration of credit cards to a digital wallet, and/or some other programmable data processing apparatus in order to produce a particular machine, such that the one or more computer-executable program code portions, which execute via the processor of the computer and/or other programmable data processing apparatus, create mechanisms for implementing the steps and/or functions represented by the flowchart(s) and/or block diagram block(s).

It will also be understood that the one or more computer-executable program code portions may be stored in a transitory or non-transitory computer-readable medium (e.g., a memory, and the like) that can direct a computer and/or other programmable data processing apparatus to function in a particular manner, such that the computer-executable program code portions stored in the computer-readable medium produce an article of manufacture, including instruction mechanisms which implement the steps and/or functions specified in the flowchart(s) and/or block diagram block(s).

The one or more computer-executable program code portions may also be loaded onto a computer and/or other programmable data processing apparatus to cause a series of operational steps to be performed on the computer and/or other programmable apparatus. In some embodiments, this produces a computer-implemented process such that the one or more computer-executable program code portions which execute on the computer and/or other programmable apparatus provide operational steps to implement the steps specified in the flowchart(s) and/or the functions specified in the block diagram block(s). Alternatively, computer-implemented steps may be combined with operator and/or human-implemented steps in order to carry out an embodiment of the present invention.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

INCORPORATION BY REFERENCE

To supplement the present disclosure, this application further incorporates entirely by reference the following commonly assigned patent applications:

| U.S. patent application Ser. No. | Title | Filed On |
|---|---|---|
| 15/802,024 | SYSTEM FOR ELECTROENCEPHALOGRAM PATTERNING RECOGNITION FOR AUTHENTICATION | Concurrently herewith |
| 15/802,036 | ELECTROENCEPHALOGRAM TRIGGERED EXPERIENCE MODIFICATION SYSTEM | Concurrently herewith |

What is claimed is:

1. A system for electroencephalogram (EEG) triggered resource distribution action control, the system comprising:
    a memory device with computer-readable program code stored thereon;
    a communication device;
    a printing device for printing the resource distribution documents;
    a processing device operatively coupled to the memory device and the communication device, wherein the processing device is configured to execute the computer-readable program code to:
        identify a transmission from an EEG reader for establishing a baseline EEG reading for the user;
        identify a transmission from the EEG reader for establishing a velocity tolerance EEG reading;
        store the baseline EEG reading for the user and the velocity tolerance EEG reading for the user in a user EEG profile;
        identify the user requesting resource distribution;
        locate an EEG reader at a location associated with the resource distribution and form a communicable linkage with the EEG reader at the location associated with the resource distribution;
        receive an EEG reading from the EEG reader at the location associated with the resource distribution;
        perform comparative spectral analysis to the EEG reading from the EEG reader at the location associated with the resource distribution;
        plot, using an EEG reading continuum, the EEG reading from the EEG reader at the location associated with the resource distribution with respect to the user baseline EEG reading and velocity tolerance EEG reading; and
        trigger action control alert distribution to a user device associated with the user upon indication of the EEG reading from the EEG reader at the location associated with the resource distribution is between the baseline EEG reading and a high velocity tolerance EEG reading on the EEG reading continuum.

2. The system of claim 1, further comprising denying and preventing a transmission of the resource distribution based on no user acknowledgement of the action control alert.

3. The system of claim 1, further comprising generating the EEG reading continuum between the baseline EEG reading for the user and velocity tolerance EEG reading for the user.

4. The system of claim 1, wherein the velocity tolerance EEG reading is an EEG reading of a user at a high and low tolerance level for resource distribution during periods of purchasing of one or more categories of products or services and an amount of resources or frequency of distribution exceeding user tolerances.

5. The system of claim 1, wherein establishing the velocity tolerance EEG reading for the user further comprises compiling EEG data during high and low tolerance level resource distribution periods and performing spectral analysis to establish the velocity tolerance EEG reading, wherein spectral analysis comprises generating a cognitive event-related biometric recognition protocol for a late potential of the EEG reading.

6. The system of claim 1, wherein establishing a baseline EEG reading for the user further comprises compiling EEG data from the baseline EEG reading and performing spectral analysis to establish the baseline EEG reading, wherein spectral analysis comprises generating a cognitive event-related biometric recognition protocol for a late potential of the EEG reading.

7. The system of claim 1, wherein establishing a baseline EEG reading for the user further comprises transmitting one or more known stimuli to the user for EEG reading of user reaction to the known stimuli to determine the user reaction to standard category resource distribution for the user.

8. A computer program product for electroencephalogram (EEG) triggered resource distribution action control with at least one non-transitory computer-readable medium having computer-readable program code portions embodied therein, the computer-readable program code portions comprising:
    an executable portion configured for identifying a transmission from an EEG reader for establishing a baseline EEG reading for the user;
    an executable portion configured for identifying a transmission from the EEG reader for establishing a velocity tolerance EEG reading;
    an executable portion configured for storing the baseline EEG reading for the user and the velocity tolerance EEG reading for the user in a user EEG profile;
    an executable portion configured for identifying the user requesting resource distribution;
    an executable portion configured for locating an EEG reader at a location associated with the resource distribution and form a communicable linkage with the EEG reader at the location associated with the resource distribution;
    an executable portion configured for receiving an EEG reading from the EEG reader at the location associated with the resource distribution;
    an executable portion configured for performing comparative spectral analysis to the EEG reading from the EEG reader at the location associated with the resource distribution;
    an executable portion configured for plotting, using an EEG reading continuum, the EEG reading from the EEG reader at the location associated with the resource distribution with respect to the user baseline EEG reading and velocity tolerance EEG reading; and an executable portion configured for triggering action control alert distribution to a user device associated with the user upon indication of the EEG reading from the EEG reader at the location associated with the resource distribution is between the baseline EEG reading and a high velocity tolerance EEG reading on the EEG reading continuum.

9. The computer program product of claim 8, further comprising an executable portion configured for denying and preventing a transmission of the resource distribution based on no user acknowledgement of the action control alert.

10. The computer program product of claim 8, further comprising an executable portion configured for generating the EEG reading continuum between the baseline EEG reading for the user and velocity tolerance EEG reading for the user.

11. The computer program product of claim 8, wherein the velocity tolerance EEG reading is an EEG reading of a user at a high and low tolerance level for resource distribution during periods of purchasing of one or more categories of products or services and an amount of resources or frequency of distribution exceeding user tolerances.

12. The computer program product of claim 8, wherein establishing the velocity tolerance EEG reading for the user further comprises compiling EEG data during high and low tolerance level resource distribution periods and performing spectral analysis to establish the velocity tolerance EEG reading, wherein spectral analysis comprises generating a cognitive event-related biometric recognition protocol for a late potential of the EEG reading.

13. The computer program product of claim 8, wherein establishing a baseline EEG reading for the user further comprises compiling EEG data from the baseline EEG reading and performing spectral analysis to establish the baseline EEG reading, wherein spectral analysis comprises generating a cognitive event-related biometric recognition protocol for a late potential of the EEG reading.

14. The computer program product of claim 8, wherein establishing a baseline EEG reading for the user further comprises transmitting one or more known stimuli to the user for EEG reading of user reaction to the known stimuli to determine the user reaction to standard category resource distribution for the user.

15. A computer-implemented method for electroencephalogram (EEG) triggered resource distribution action control, the method comprising:
providing a computing system comprising a computer processing device and a non-transitory computer readable medium, where the computer readable medium comprises configured computer program instruction code, such that when said instruction code is operated by said computer processing device, said computer processing device performs the following operations:
identifying a transmission from an EEG reader for establishing a baseline EEG reading for the user;
identifying a transmission from the EEG reader for establishing a velocity tolerance EEG reading;
storing the baseline EEG reading for the user and the velocity tolerance EEG reading for the user in a user EEG profile;
identifying the user requesting resource distribution;
locating an EEG reader at a location associated with the resource distribution and form a communicable linkage with the EEG reader at the location associated with the resource distribution;
receiving an EEG reading from the EEG reader at the location associated with the resource distribution;
performing comparative spectral analysis to the EEG reading from the EEG reader at the location associated with the resource distribution;
plotting, using an EEG reading continuum, the EEG reading from the EEG reader at the location associated with the resource distribution with respect to the user baseline EEG reading and velocity tolerance EEG reading; and
triggering action control alert distribution to a user device associated with the user upon indication of the EEG reading from the EEG reader at the location associated with the resource distribution is between the baseline EEG reading and a high velocity tolerance EEG reading on the EEG reading continuum.

16. The computer-implemented method of claim 15, further comprising denying and preventing a transmission of the resource distribution based on no user acknowledgement of the action control alert.

17. The computer-implemented method of claim 15, further comprising generating the EEG reading continuum between the baseline EEG reading for the user and velocity tolerance EEG reading for the user.

18. The computer-implemented method of claim 15, wherein the velocity tolerance EEG reading is an EEG reading of a user at a high and low tolerance level for resource distribution during periods of purchasing of one or more categories of products or services and an amount of resources or frequency of distribution exceeding user tolerances.

19. The computer-implemented method of claim 15, wherein establishing the velocity tolerance EEG reading for the user further comprises compiling EEG data during high and low tolerance level resource distribution periods and performing spectral analysis to establish the velocity tolerance EEG reading, wherein spectral analysis comprises generating a cognitive event-related biometric recognition protocol for a late potential of the EEG reading.

20. The computer-implemented method of claim 15, wherein establishing a baseline EEG reading for the user further comprises compiling EEG data from the baseline EEG reading and performing spectral analysis to establish the baseline EEG reading, wherein spectral analysis comprises generating a cognitive event-related biometric recognition protocol for a late potential of the EEG reading.

\* \* \* \* \*